United States Patent

Ross

[11] Patent Number: 6,102,254
[45] Date of Patent: Aug. 15, 2000

[54] PHARMACEUTICAL COMPOSITIONS IN SEMISOLID FORM AND A DEVICE FOR ADMINISTRATION THEREOF

[75] Inventor: Malcolm Stewart Frank Ross, Tel Aviv, Israel

[73] Assignee: Taro Pharmaceutical Industies Ltd., Haifa Bay, Israel

[21] Appl. No.: 09/251,155

[22] Filed: Feb. 17, 1999

Related U.S. Application Data

[63] Continuation of application No. 08/114,315, Aug. 30, 1993, Pat. No. 5,881,926, which is a continuation-in-part of application No. 08/029,443, Mar. 11, 1993, abandoned.

[51] Int. Cl.[7] .................................................. B67D 5/56
[52] U.S. Cl. .................... 222/192; 222/212; 222/153.06; 141/18; 141/114
[58] Field of Search .................................. 222/192, 106, 222/205, 207, 212, 153.06, 153.14, 515, 541, 549; 73/426, 429; 141/18, 25, 114

[56] References Cited

U.S. PATENT DOCUMENTS

| | | |
|---|---|---|
| 1,466,043 | 8/1923 | Graham . |
| 1,544,232 | 6/1925 | Huntoon . |
| 2,252,119 | 8/1941 | Edmonds .................................... 141/25 |
| 2,556,571 | 7/1951 | Bobbs et al. . |
| 2,559,070 | 1/1951 | Goldberg ................................ 222/515 |
| 3,104,032 | 9/1963 | Hansen . |
| 3,116,152 | 12/1963 | Smith et al. . |
| 3,133,679 | 5/1964 | Brown ..................................... 222/205 |
| 3,145,886 | 8/1964 | Goodwin . |
| 3,383,018 | 5/1968 | Grimsley . |
| 3,395,835 | 8/1968 | Tarran ..................................... 222/205 |
| 3,493,146 | 2/1970 | Cones et al. ....................... 222/153.06 |
| 3,767,784 | 10/1973 | Gluck . |
| 3,797,704 | 3/1974 | Dykes ................................ 222/153.14 |
| 3,920,819 | 11/1975 | Stephens et al. . |
| 3,927,205 | 12/1975 | Ohno et al. . |
| 4,091,965 | 5/1978 | Gebhard . |
| 4,284,649 | 8/1981 | Wiczer . |

(List continued on next page.)

FOREIGN PATENT DOCUMENTS

| | | |
|---|---|---|
| 0 189 722 | 8/1986 | European Pat. Off. . |
| 0 379 147 | 7/1990 | European Pat. Off. . |
| 0 479 005 | 4/1992 | European Pat. Off. . |
| 0 839 517 A2 | 1/1998 | European Pat. Off. ......... A61K 7/16 |
| 9 815 854 A1 | 1/1998 | European Pat. Off. ......... A61K 9/48 |
| 798900 | 7/1958 | United Kingdom . |
| WO 96/23486 | 8/1996 | WIPO .............................. A61K 9/00 |

*Primary Examiner*—Philippe Derakshani
*Attorney, Agent, or Firm*—Michael A. Gollin; Venable

[57] ABSTRACT

A pharmaceutical delivery system for oral administration of a pharmaceutical agent comprises: (a) a squeezable container having an outlet defining a flow channel, (b) a channel closure device adapted to selectively close or open the flow channel; and (c) within the container, at least one dose of a pharmaceutical composition, the composition being a semisolid material that is storage stable, and consists of mutually compatible components, the components comprising (i) an effective amount of an orally active pharmaceutical agent useful for systemic treatment, and (ii) a palatable pharmaceutically acceptable vehicle, comprising a liquid base selected from the group consisting of water, propylene glycol, polyethylene glycol, glycerin, and mixtures thereof, a thickening agent selected from the group consisting of starch, modified starch, sodium carboxymethyl cellulose, microcrystalline cellulose, hydroxypropyl cellulose, hydroxypropyl methylcellulose, other cellulose derivatives, acacia, tragacanth, pectin, gelatin, polyethylene glycol, and water-soluble carboxyvinyl polymers, the pharmaceutical composition having a consistency which allows the composition to be squeezed by manual pressure through the flow channel, whereby in response to pressure on the container when the flow channel is open, a predetermined unit dose of the pharmaceutical composition can be easily squeezed from the container into a receptacle, measured, and administered orally without spilling any of the composition from the container or the receptacle.

47 Claims, 7 Drawing Sheets

U.S. PATENT DOCUMENTS

| | | |
|---|---|---|
| 4,305,933 | 12/1981 | Wiczer . |
| 4,361,580 | 11/1982 | Peck et al. . |
| 4,383,993 | 5/1983 | Hussain et al. . |
| 4,394,390 | 7/1983 | Hussain et al. . |
| 4,427,681 | 1/1984 | Munshi . |
| 4,540,572 | 9/1985 | Seth . |
| 4,576,645 | 3/1986 | Ravel et al. . |
| 4,593,048 | 6/1986 | Sato et al. . |
| 4,651,905 | 3/1987 | Hayes ............ 222/515 |
| 4,724,615 | 2/1988 | Mackles et al. . |
| 4,761,400 | 8/1988 | Doat et al. . |
| 4,830,222 | 5/1989 | Read . |
| 4,883,660 | 11/1989 | Blackman et al. . |
| 4,957,226 | 9/1990 | Pacia ............ 222/205 |
| 4,964,538 | 10/1990 | Nimmey et al. . |
| 5,137,183 | 8/1992 | Mikulec et al. . |
| 5,154,926 | 10/1992 | Kawasaki et al. . |
| 5,288,479 | 2/1994 | Gorman et al. . |
| 5,300,302 | 4/1994 | Tachon et al. . |
| 5,305,928 | 4/1994 | Verdaguer ............ 222/205 |
| 5,602,182 | 2/1997 | Popli et al. ............ 514/653 |
| 5,881,926 | 3/1999 | Ross ............ 222/192 |

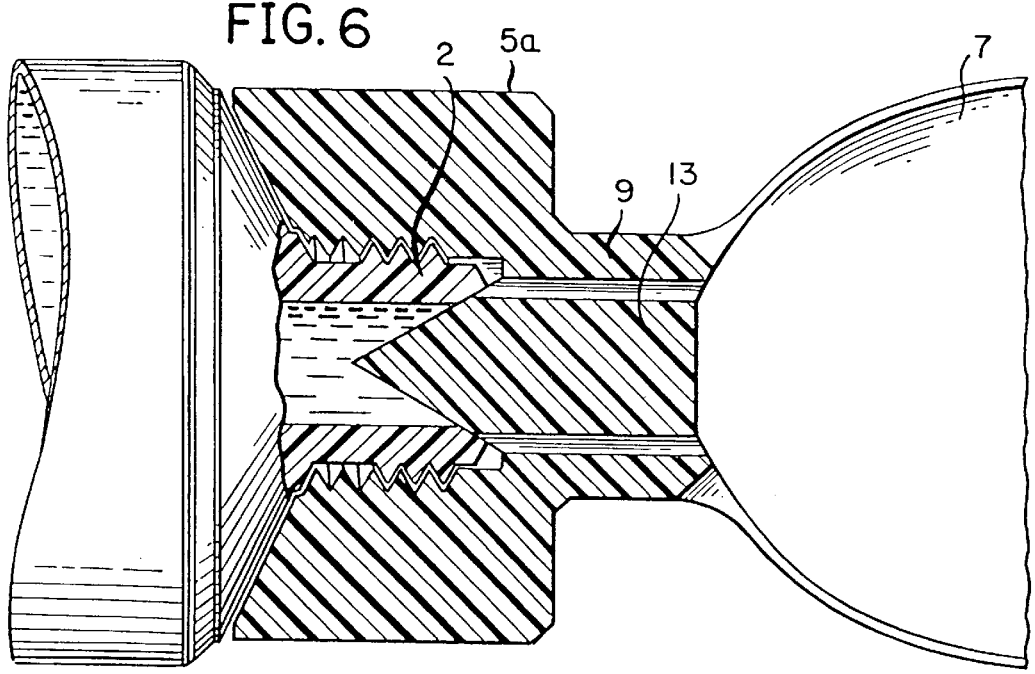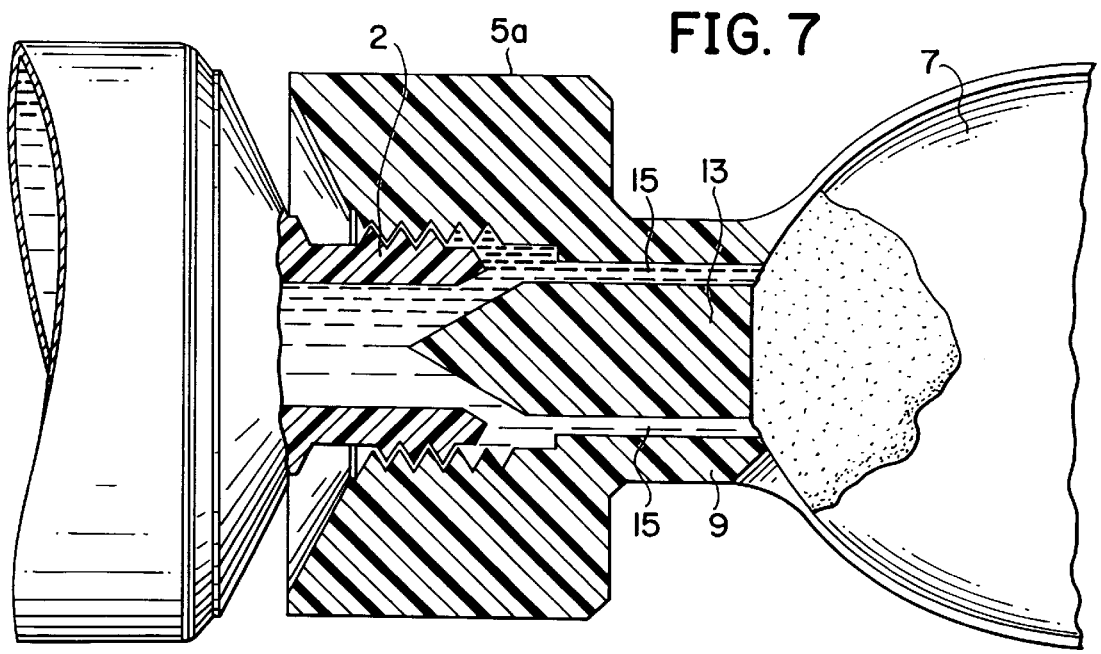

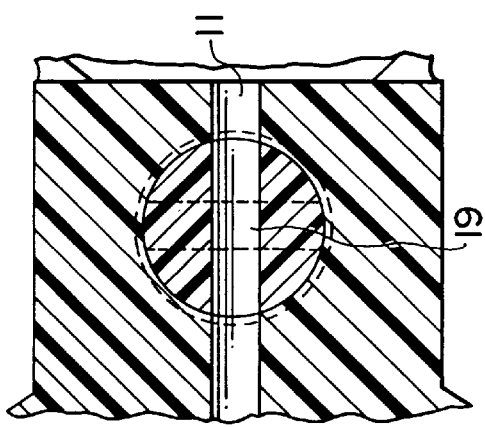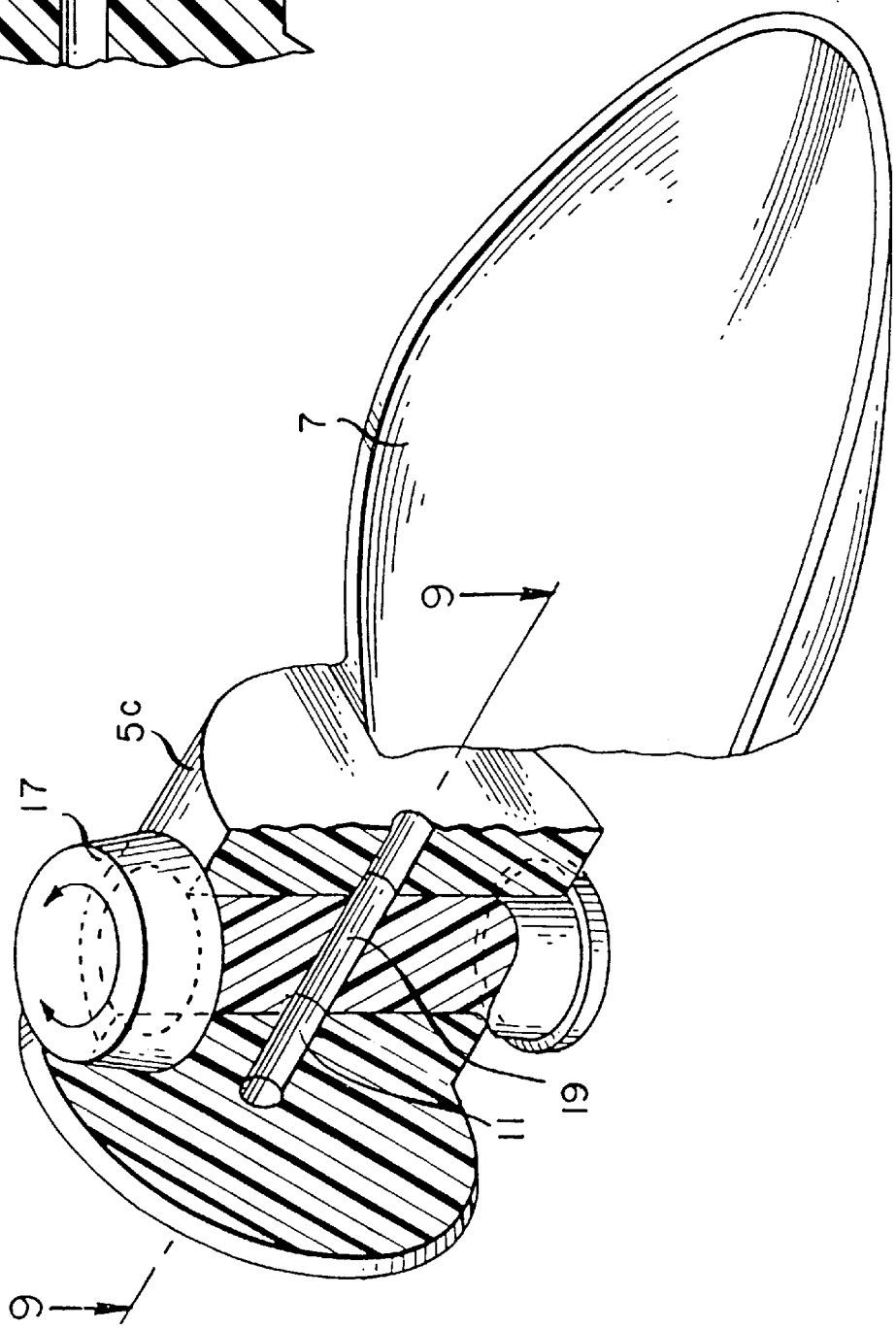

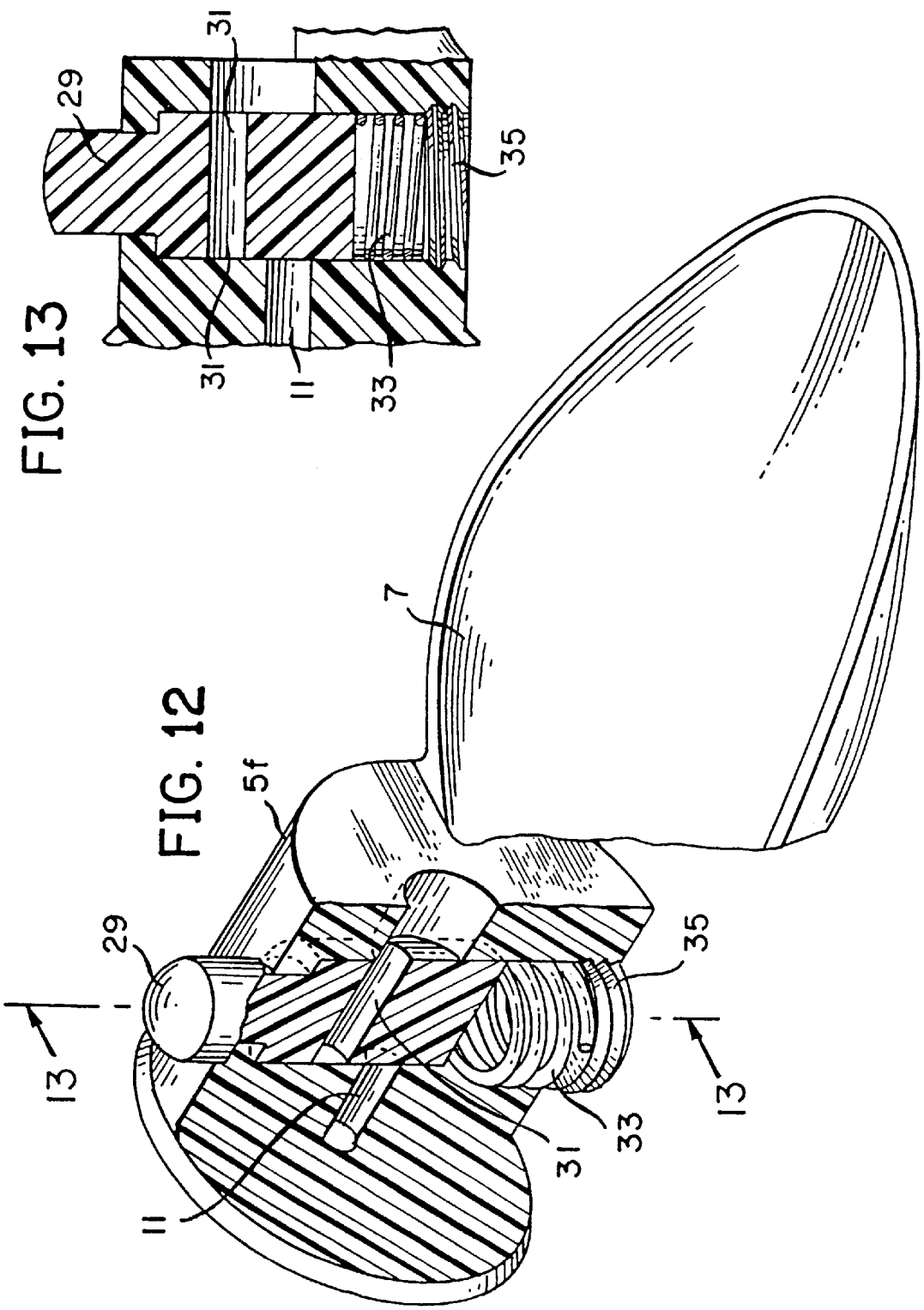

PHARMACEUTICAL COMPOSITIONS IN SEMISOLID FORM AND A DEVICE FOR ADMINISTRATION THEREOF

This application is a continuation of application No. 08/114,315, filed Aug. 30, 1993, now U.S. Pat. No. 5,881,926, which is a continuation-in-part of copending application Ser. No. 08/029,443, filed Mar. 11, 1993 now abandoned.

BACKGROUND OF THE INVENTION

This invention is concerned with new formulations of orally active pharmaceutical agents and a device for administration thereof. More particularly this invention is concerned with formulations in semisolid form for oral administration of pharmaceutical agents used for systemic treatment, preferably contained in a single dose packet or in a multi-dose measuring device which can be used to measure as well as to administer the formulation, and to a childproof closure useful for the device.

Heretofore, pharmaceutical agents for systemic treatment by oral administration have generally been formulated in solid form as pills or capsules or in liquid form. Children, the elderly and people with motor problems often have problems swallowing pills and capsules. It is also difficult to administer medicine in liquid form to children, even when the liquid has been thickened to a syrup, and the elderly and those with motor problems also have difficulty with the self administration of liquid, especially when it is necessary to measure a specific unit dose.

Important requirements for a non-solid pharmaceutical formulation for oral administration include palatability to children and adults, stability, i.e. a long shelf life, compatibility of formulation components with active agent and desirably, ease of administration of the required dose.

Pharmaceutical preparations in semisolid form for topical application are well known in the art. Such preparations include gels, pastes, creams and ointments for use on the skin, teeth and mucous membranes. Antacids and anti-ulcer agents in suspension and gel form for coating the mucous lining of the stomach are also well known in the art.

In a few instances, systemically useful pharmaceutical agents have been incorporated into gelled vehicles, as for example those disclosed in U.S. Pat. Nos. 4,305,933, 4,576,645 and 4,883,660. However, these vehicles all suffer from one or more disadvantages, such as the presence of a component which is undesirable for administration to children and/or is incompatible with many pharmaceutical agents, the presence of an emulsion which is difficult to manufacture and tends to be unstable and/or inadequate viscosity.

There is a need for an economical formulation of systemic pharmaceutical agents in easily-administered form, as well as a need for easily administered non-spill pharmaceutical formulations which can be measured and administered effortlessly to children and by adults with motor problems. There is also a need for a simple to use and easily manufactured device for the measurement and administration of a predetermined dose of a pharmaceutical agent and also for a device of this type which is substantially tamper-proof in so far as young children or individuals with limited mental capacity are concerned.

While devices for dispensing a measured amount of a composition have been disclosed, for example in U.S. Pat. Nos. 3,104,032 and 3,383,081, these devices tend to be complicated and are not completely satisfactory for easy delivery and administration of a measured amount of a pharmaceutical composition.

SUMMARY OF THE INVENTION

An object of the invention is the provision of pharmaceutical agents useful for systemic treatment by the oral route in a form which is convenient to administer to children and which is convenient for self administration of aging adults, as well as adults with motor problems.

Another object of the invention is the provision of pharmaceutical agents useful for systemic treatment by oral administration in a composition which is provided in a device from which it is particularly easy to administer and convenient to measure single dosage units of the composition.

A further object of the invention is the provision of pharmaceutical agents useful for systemic treatment by oral administration in a form which avoids the problems of liquid formulations, such as spillage.

Another important object of the invention is the provision of a device for easily administering pharmaceutical formulations in semisolid form in dosage units.

Still another important object of the invention is the provision of a device for easily administering pharmaceutical formulations in semisolid form in dosage units which is substantially tamper proof by young children or individuals with limited mental capacity.

A further important object of the invention is the provision of a childproof closure useful for a device for holding pharmaceutical formulations.

These and other objects of the invention are achieved by the invention set forth below.

It has been discovered that pharmaceutical agents in semisolid form, such as a gel or paste, are much easier to administer to children than liquid and solid dosage forms and are much easier for an aging adult or a adult with motor problems to measure than a liquid and in some cases are easier to swallow than a pill or capsule. It has also been discovered that such compositions can be desirably packaged in a single dosage form or in a multi-dose device which contains measuring and administration means.

According to the invention, a pharmaceutical agent useful for oral administration to treat an illness systemically is provided as a semisolid in gel or suspension form, such as a paste, in a composition containing the pharmaceutical agent and a pharmaceutically acceptable vehicle comprising a thickening agent and a liquid base compatible with the pharmaceutical agent and thickening agent in which the pharmaceutical agent is soluble.

In a preferred embodiment of the invention, a single dose of the semisolid pharmaceutical composition is contained in a flexible packet which can be opened by tearing or cutting.

In another preferred embodiment of the invention, a device for containing the semisolid pharmaceutical composition is provided which comprises a squeezable container with means for measuring and administering therefrom a single dose of the semisolid composition of the invention and resealing the container thereafter.

In a particularly preferred embodiment of the invention, a device for containing multiple doses and measuring a single dose of the semisolid composition of the invention comprises a squeezable container for holding the pharmaceutical composition having an open neck with exterior threads for attaching a cap thereto and a cap with interior threads suitable to engage the outer threads of the neck of the squeezable container, a spoon having a shaft with channel means fixed in the cap so that the bowl-shaped end of the spoon projects outside the cap and the shaft projects into the cap and the channel means are in alignment with the open neck of the squeezable container and sealing means in said cap positioned to seal the container when the cap is fully closed and to provide space for the contents of the container to flow through the channel means into the spoon in response to pressure on the container when the cap is partially opened, whereby contents of the squeezable container can be squeezed into the bowl-shaped end of the spoon and administered therefrom.

The device of the invention can be resealed after use by including any of a variety of resealing means in the cap, such as pin inside the cap which rests against and closes the neck of the squeezable container when the cap is tightened after use; a rotatable or pivotable valve and a spring activated step valve, which allow passage of the semisolid composition from the tube to the spoon when open and seal off the contents of the squeezable container when in the closed position.

Another embodiment of the invention is a closure which cannot be normally opened normally by a child, which is referred to herein as a childproof closure, and which can be used in the device of the invention.

BRIEF DESCRIPTION OF THE DRAWINGS

FIG. 6, which illustrates the cap in closed position and

FIG. 7, which illustrates the cap in open position with semisolid composition of the invention being squeezed into the spoon, show sections of the cap of FIG. 5 taken along the line 7—7.

FIG. 8 is a perspective view of a cap, partially broken away to reveal the inner structure of the resealing mechanism of another embodiment of the device of the invention;

FIG. 9 shows a section of the cap of FIG. 8 taken along the line 9—9.

FIG. 12 is a perspective view of a cap, partially broken away to reveal the inner structure of a cap with a spring-activated mechanism of another embodiment of the device of the invention;

FIG. 13 shows a section of FIG. 13 along the line 13–13.

DESCRIPTION OF THE INVENTION

Figure 2:
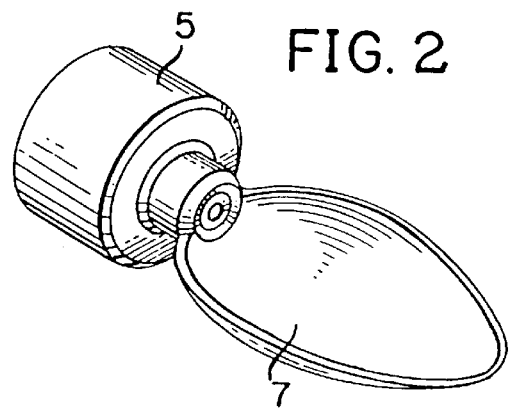
FIG. 2 illustrates a replacement cap of the invention for the tube of FIG. 1 equipped with a spoon for measuring and administering a dose of the semisolid composition of the invention.
Figure 1:
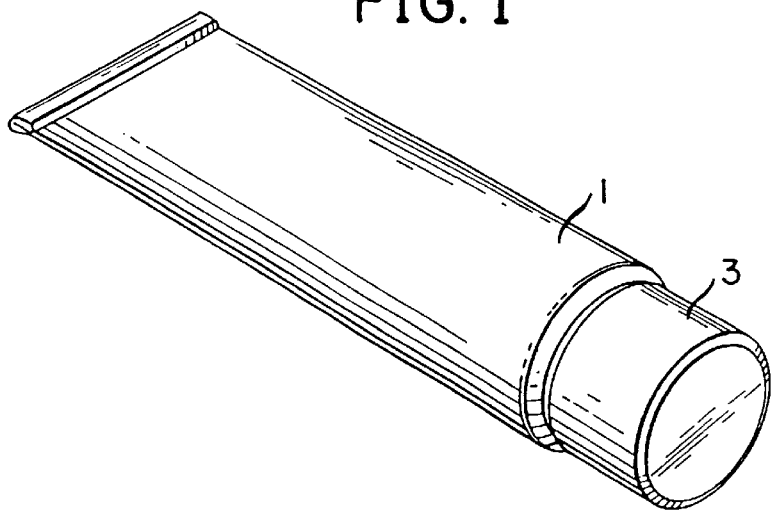
FIG. 1 illustrates a closed tube containing a semisolid composition of the invention.

The pharmaceutical compositions of the invention are comprised of a pharmaceutical agent in an effective amount for systemic treatment by oral administration in admixture with a pharmaceutically acceptable vehicle comprising a thickening agent in a amount which provides a semisolid, such as a gel or a paste suspension. The semisolid has a Brookfield viscosity at of above 2500 cps, preferably 2500 to 70,000 cps more preferably 3500–65,000 cps and most preferably about 7,500–40,000 cps. In the present application, viscosity refers of Brookfield viscosity, measured at 25° C. and a spindle speed of 10 rpm, unless otherwise noted.

The semisolid form is generally a gel or a paste suspension which has the required viscosity to be squeezed easily through a small orifice similarly to tooth paste, dermatological creams, ointments and the like. The particular viscosity above 2500 cps is not critical as long as it fulfills the requirement of being a semisolid which is squeezable through a relatively small orifice such as that usual at the mouth of a flexible tube.

In general, the viscosity of the compositions of the invention can be varied by the choice and amount of thickening agent used from about 2500 cps to any greater viscosity which still permits the composition to be readily squeezed through a relatively narrow orifice, i.e. of the order of about 1 to 5 mm in diameter, such as that provided by the opening of a single dose packet or a seal-a-spoon device of the invention.

By systemic treatment is meant treatment which affects the body as a whole, as compared to topical treatment, which affects only that part of the body to which it is applied, i.e. skin, teeth or particular mucous membrane, such as the lining of the stomach.

Orally active pharmaceutical agents which may be present in the semisolid compositions of the invention are those useful for systemic treatment by oral administration and include for example:

analgesics, such as acetaminophen, codeine, aspirin and dihydrocodeinone;

anti-inflammatory agents, such as ibuprofen, naproxen and diclofenac;

anti-histamines including $H_1$-blockers, such as chlorpheniramine, terfenadine, loratidine, astemizole and cetirizine and $H_2$-blockers, such as cimetidine and ranitidine;

anti-infectives including: antibacterials such as sulfa drugs, i.e. sulfisoxazole; quinolones, i.e. ciprofloxacin and ofloxacin; tetracyclines, i.e. tetracycline; anti-virals, i.e acyclovir and amantadine and anti-fungals, i.e. fluconozole;

bronchodilators, such as albuterol, metaproterenol and theophylline;

cough suppressants, such as dextromethorphan;

expectorants, such as guaifenesin;

CNS active agents, including: hypnotics, such as triazolam; sedatives, such as phenobarbital; tranquilizers, such as chlorpromazine and diazepam; antidepressants, such as fluoxetine and nortriptylline; anti-convulsants, such as carbamazepine and ethosuximide and anti-Parkinson's agents, such as L-DOPA;

cardiovascular drugs including: diuretics, such as hydrochlorthiazide; anti-hypertensives including: beta-blockers, such as propranolol; ACE inhibitors, such as captopril and enalapril; calcium channel blockers, such as diltiazem; anti-anginals, same as anti-hypertensive agents; cardiac glycosides, such as digoxin;

antineoplastics, such as 5-fluorouracil and cyclophosphamide;

cholesterol-lowering agents such as lovastatin;

anti-emetics, such as metoclopramide;

vitamins, such as A, $B_1$, $B_6$, C, $D_3$ and E;

minerals, such as iron, calcium and zinc salts and fecal softeners, such as docusate.

Useful pharmaceutical agents of course include pharmaceutically acceptable salts and esters of the named compositions.

The semisolid compositions of the invention have a liquid base, which is a palatable pharmaceutically acceptable solvent, preferably a solvent which dissolves the active pharmaceutical agent. Preferred solvents include water, propylene glycol, glycerin and mixtures thereof. In some instances it may be necessary to include a compound which is effective to solubilize the active pharmaceutical agent in the solvent, for example, lactic acid is used in an aqueous formulation of ciprofloxacin hydrochloride to solubilize this active ingredient.

According to the invention, any pharmaceutically acceptable thickening agent can be used in the compositions of the invention, providing of course that the thickening agent is compatible with the active agent and the solvent base. Examples of useful thickening agents include natural occurring thickening agents or thickening agents derived from naturally occurring materials, such as starch and starch derivatives, for example modified starch; cellulose derivatives, for example sodium carboxymethylcellulose, microcrystalline cellulose and hydroxypropyl cellulose; acacia; tragacanth, pectin and gelatin, as well as totally synthetic thickening agents, such as polyethylene glycol and water soluble carboxyvinyl polymers, such as those sold under the names of carbomer and Carbopol™, which is produced by B. F. Goodrich Chemical Group. Gelatin, cellulose derivatives, polyethylene glycols and water soluble carboxyvinyl polymers are preferred.

A sweetener is added to the composition of the invention in an amount necessary to make the semisolid palatable.

Ingredients such as flavoring, coloring matter, filler, preservative, buffer, sodium chloride and carriers usual in pharmaceutical compositions can also be present in the semisolid compositions of the invention.

In one preferred embodiment, a single dose of the semisolid pharmaceutical composition of the invention is contained in a small flexible packet or sachet which is readily torn or cut so that the contents thereof can be squeezed directly into the mouth, or if preferred, into another vehicle for oral administration. Such a containers are commonly used, for example, for single servings of condiments and can be made of flexible plastic and/or of non-corrosive metal film.

In another preferred embodiment, multiple doses of the semisolid pharmaceutical composition of the invention are contained in a device of the invention referred to as a seal-a-spoon which is described in detail below and in the accompanying drawings.

Figure 3:
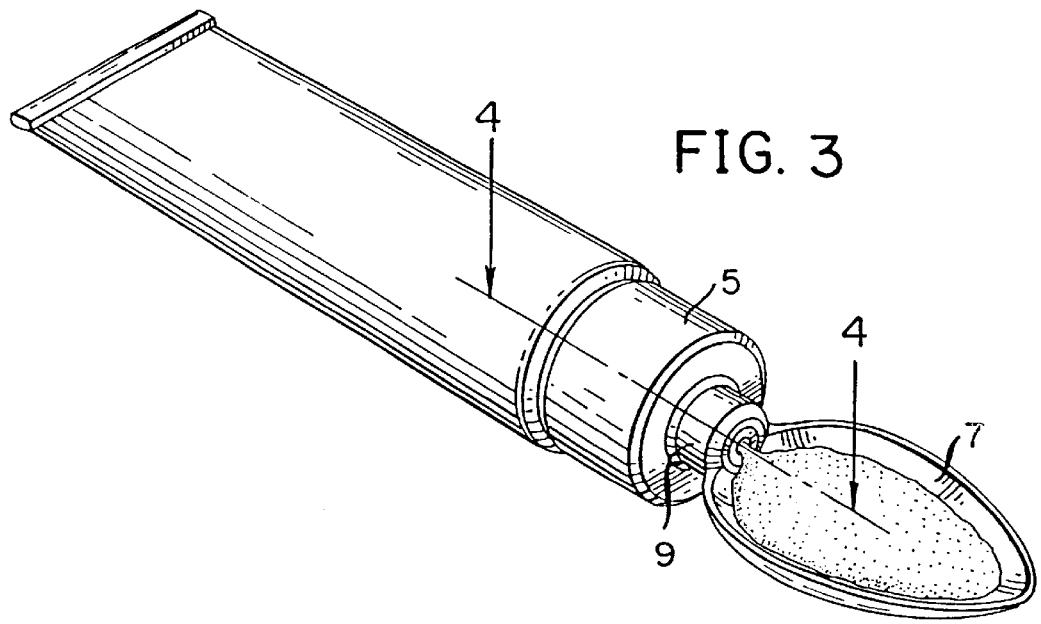
FIG. 3 illustrates a tube containing the semisolid composition of the invention with attached replacement cap equipped with a spoon and FIG. 4 shows a section of FIG. 3 along lines 4—4.
Figure 4:
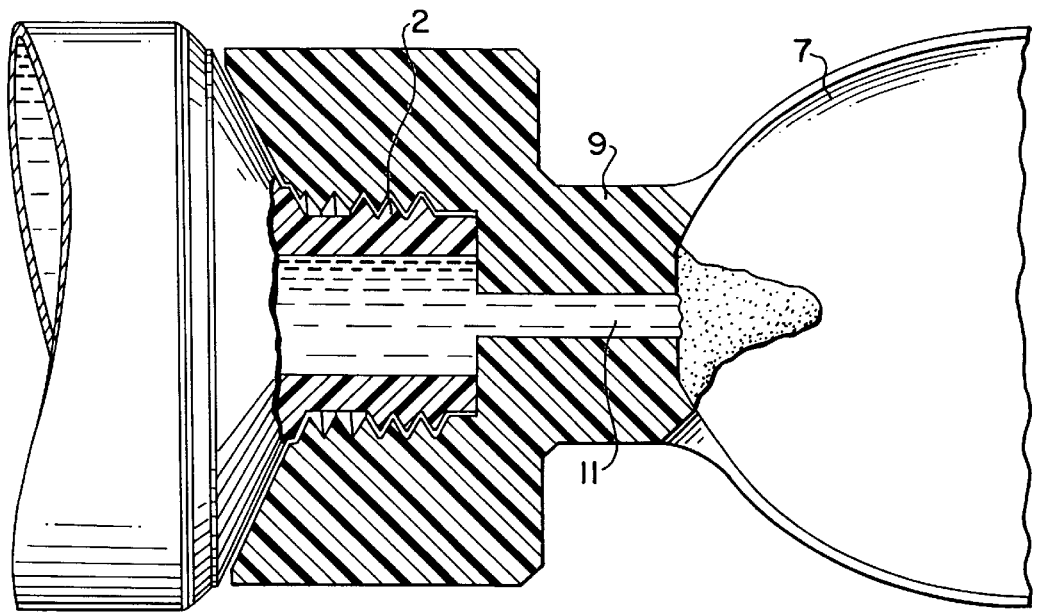

With reference to FIGS. 1–4, the tube 1 containing a semisolid pharmaceutical composition of the invention is provided with the cap 3, which can be replaced by the cap 5 shown in FIG. 2. The device with attached cap 5 is illustrated in FIGS. 3 and 4. As is usual, the outside of neck 2 of tube 1 and the inside of cap 5 are provided with corresponding threads, so that the cap can be fixed to the neck of the tube. A spoon shaped projection 7, which is preferably sized to contain a single unit dose of the semisolid composition of the invention contained in tube 1, is connected to the cap 5 by means of the shaft 9, which is provided with a channel 11 adapted to be aligned with the opening of the neck 2 of tube 1, so that the semisolid composition in tube 1 can be squeezed directly from the tube 1 through the channel 11 into the spoon shaped projection 7 and administered therefrom.

Figure 16:
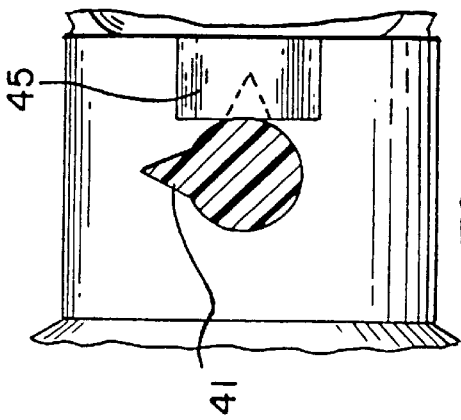
Figure 15:
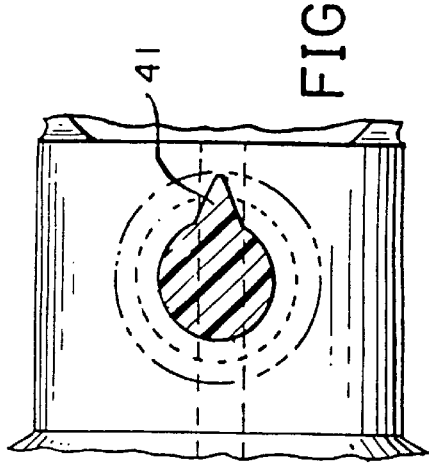
FIG. 15 shows a section of FIG. 14 taken along line 15—15 which illustrates means to prevent access of the contents of the tube to children and FIG. 16 also shows a section of Figure taken along line 15—15 which illustrates means to prevent tampering of the device prior to intended use.
Figure 14:
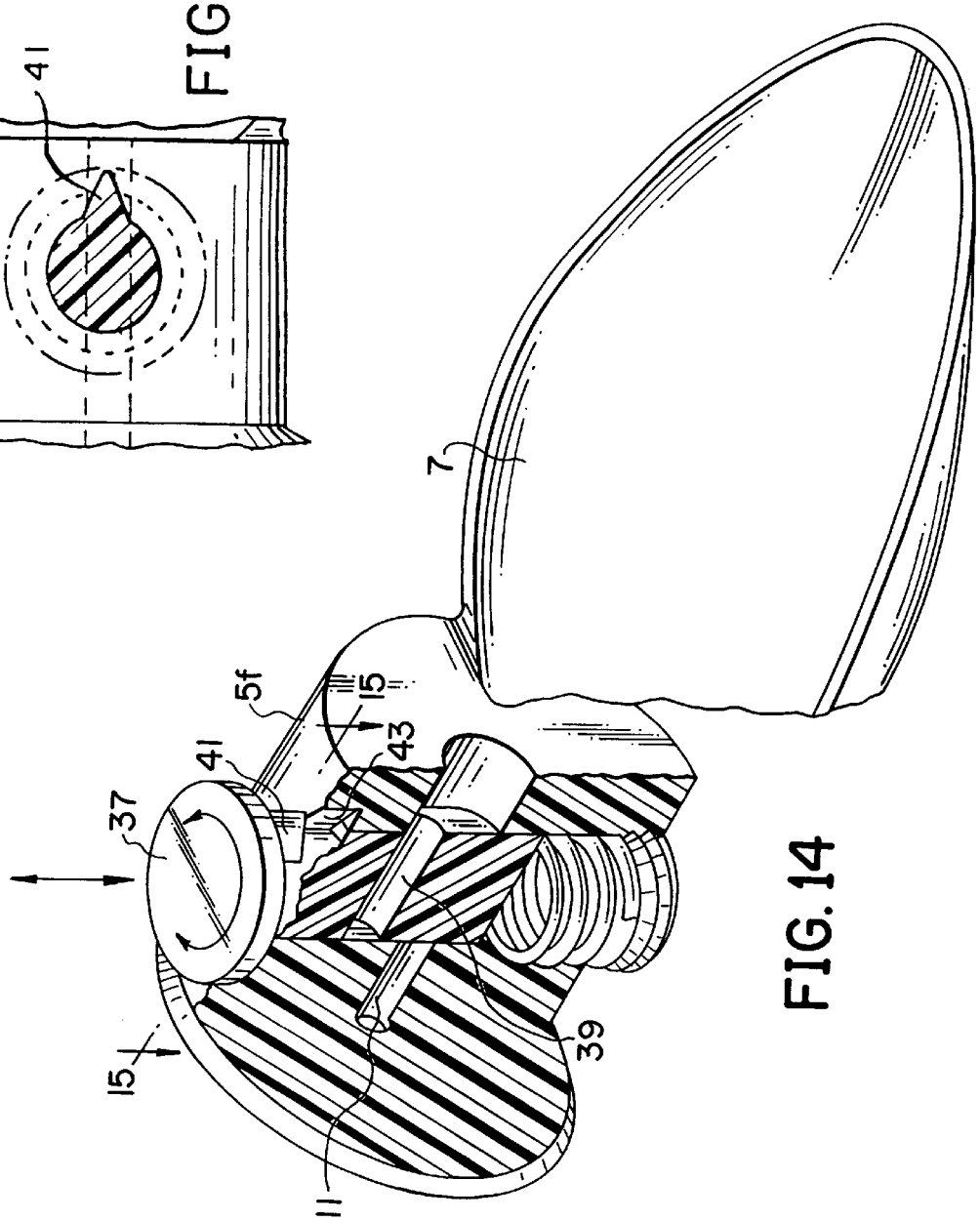
FIG. 14 is another perspective view of a cap, partially broken away to reveal the inner structure of resealing means with a spring-activated mechanism of another embodiment of the device of the invention, which is further provided with means to prevent access of the contents of the tube to children and to prevent tampering.

Seal-a-spoon devices of the invention wherein the cap containing the spoon-shaped projection is provided with resealable means are illustrated in FIGS. 5–15. A seal-a-spoon device of the invention with a "child-proof" mechanism and also with tamper-proof means is illustrated in FIGS. 14–16.

Figure 5:
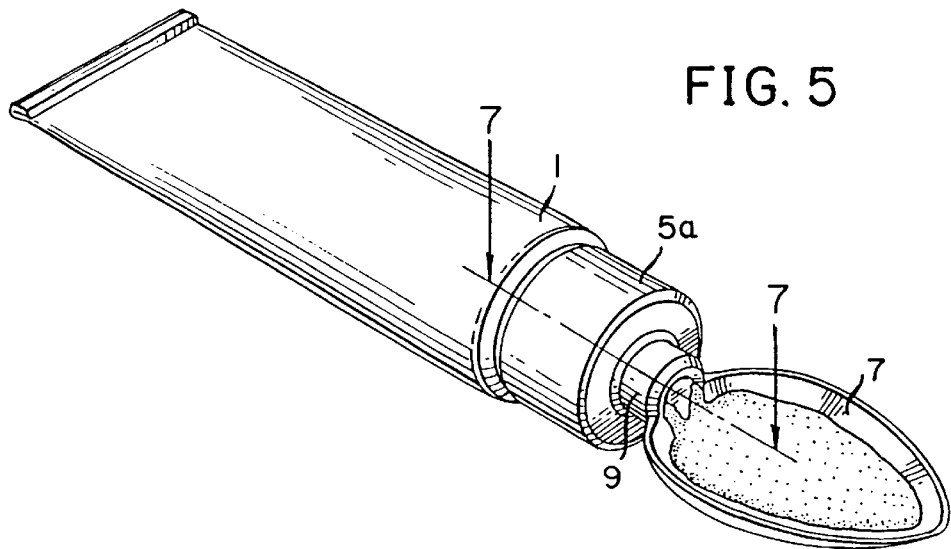
FIG. 5 illustrates an alternate device of the invention having a resealable cap equipped with a spoon.

As illustrated in FIGS. 5–7, the spoon shaped projection 7 set in cap 5a by shaft 9 is provided with a pin 13 which projects into the inside of the cap 5a and is adapted to rest against the neck 2 of tube 1 and seal the tube when the cap 5a is in the fully closed position illustrated in FIG. 6. When the cap is rotated a few notches, as illustrated in FIG. 7, but not separated from tube 1, the pin no longer rests against the neck of tube 1, which is then unsealed and the semisolid composition in tube 1 can be readily forced through the channel 15, which is present between the shaft 9 and the pin 13, into the projecting spoon 7 and administered directly therefrom.

Another embodiment of the seal-a-spoon device of the invention is illustrated in FIGS. 8 and 9 wherein the cap 5c is provided with the rotating valve or stopcock 17 having a channel 19 which can be aligned as shown with the channel 11 in the shaft 9 (not shown) or turned to prevent the flow of semisolid composition from the tube 1, as indicated by the dashed line in FIG. 9.

Figure 10:
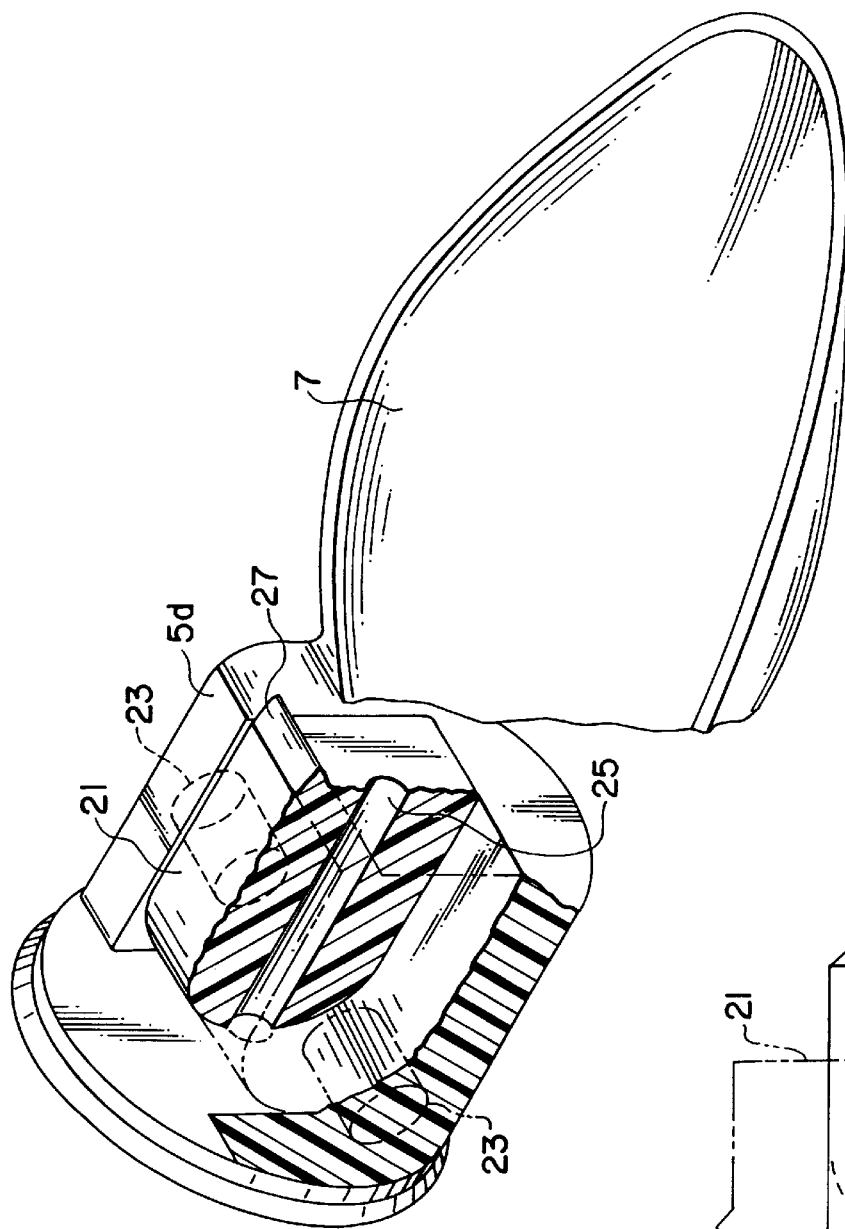
FIG. 10 is a perspective view of a cap, partially broken away to reveal the inner structure of the pivoting valve resealing mechanism of another embodiment of the device of the invention.
Figure 11:
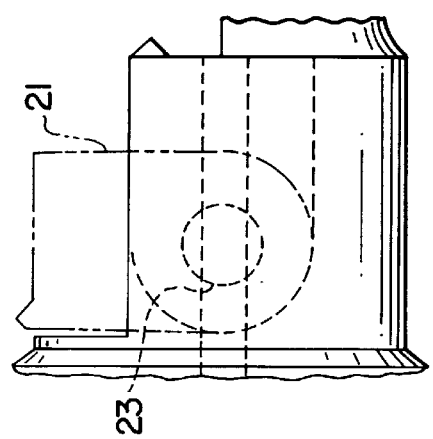
FIG. 11 is a partial side view of the pivoting valve with a phantom outline of the pivoting valve in the upright closed position shown by the dash-dot line and the open position by the dashed line.

Still another embodiment of the seal-a-spoon device of the invention is illustrated in FIGS. 10 and 11, wherein the cap 5d is provided with the pivoting valve 21 connected to the pivoting hinge 23. The pivoting valve 21 has a channel 25 which is in alignment with the channel 11 of the shaft 9 (not shown) when in the down position illustrated, allowing the flow of semisolid composition from the tube 1 (not shown) into the spoon 7; when the pivoting valve 21 is moved to the upright position, as shown by the dash-dot line of FIG. 11, with the aid of the protuberance 27, the contents of the tube 1 are resealed.

Further embodiments of the seal-a-spoon device of the invention are illustrated in FIGS. 12–15. As shown in FIGS. 12 and 13, the cap 5e is provided with a spring biased step cylinder 29 having a channel 31; the spring 33 is held in place by a retaining member 35, such as a screw plug. When the step cylinder 29 is in the normal upright position, the contents of tube 1 (not shown) are sealed; when the step cylinder 29 is pressed to compress the spring 33, so that the channel 31 is in alignment with the channel 11 of the shaft 9 (not shown), the contents of the tube 1 (not shown) can be squeezed into the spoon 7.

A childproof and tamper proof seal-a-spoon device of the invention is illustrated in FIGS. 14–16, wherein the cap 5f is provided with a rotating spring biased step cylinder 37 having a channel 39 and also having on its side, near the top, the button 41. The cap 5f is also provided on its outside near the step cylinder 37, with a cavity 43 corresponding in size and shape to the button 41. When the step cylinder 37 is in the normal upright position, the contents of the tube 1 (not shown) are sealed. The step cylinder 37 cannot be depressed unless the button 41 is lined up with the cavity 43 in the cap 5f. In addition, the cavity in the cap 5f is initially sealed with a sheet of plastic 45. When the button is aligned with the cavity of corresponding shape in the cap 5f and pushed for the first time, the plastic sheet 45 is broken. An unbroken sheet 45 means that the cap 5f has not been previously used or tampered with. The cap 5f is a permanent cap which can not be removed by normal means or which has special safeguards against removal.

Since the rotating spring biased cylinder 37 cannot be depressed unless the button 41 is first lined up with the cavity 43 in the cap 5f, three different motions are required before the contents of the tube 1 (not shown) can be caused to flow into the spoon 7: aligning the button 41 with the cavity 43 by rotating the step cylinder 37, depressing the step cylinder 37 to align the channel 39 with channel 11 and pressing on the tube 1 to effect the flow of semisolid composition from the tube to the spoon 7. Therefore, this embodiment of the seal-a-spoon device of the invention is considered to be child proof, as well as tamper proof.

The childproof closure illustrated in FIG. 14, with or without (not illustrated) the projecting spoon, can be applied to other containers of medicine.

The following examples further illustrate the invention, but must not be construed as limiting the invention in any manner.

EXAMPLE 1

Acetaminophen Formulation Thickened with Polyethylene Glycols

Acetaminophen was dissolved in a minimum quantity of water and combined with propylene glycol, a mixture of polyethylene glycols (PEG 400, which has an average molecular weight of Boo and PEG 3350, which has an average molecular weight of 1600), preservative, sweetener and flavoring to provide the following composition in percent by weight.

| | |
|---|---|
| PEG mixture | 72 |
| Acetaminophen | 2.5 |
| Propylene glycol | 25 |
| Methylparabens | 0.22 |
| Sodium Saccharin | 0.2 |
| Cherry essence | 0.05 |
| Red DC 33 | 0.005 |
| Water | to 100 |

PEG mixtures were varied in the foregoing formula to provide compositions with different viscosities as shown in Table 1. The viscosities were measured by means of a Brookfield Viscometer at 20° C. at a spindle speed of 20 to 100 rpm, depending on medium viscosity, or at 25° C. at a spindle speed of 10 rpm. All of these compositions are useful as semisolids for oral administration and can be packed in single dose containers or-in a multiple dose device of the invention.

TABLE 1

| PEG 400 % by wt. | PEG 3350 % by wt | VISCOSITY CPS |
|---|---|---|
| 60 | 40 | 62,640 |
| 70 | 30 | 39,280 |
| 80 | 20 | 25,040 |

EXAMPLE 2

Pseudoephedrine HCl Formulation Thickened with Polyethylene Glycols

Pseudoephedrine HCl (0.6%) is incorporated into a formulation base consisting of propylene glycol (25%), polyethylene glycols (73.5%) consisting of 75% PEG 400 and 25% PEG 3350, methyl parabens (0.22%) as a preservative, sodium saccharin (0.2%) as a sweetener, coloring and flavoring matter and water to make 100%.

This formulation provides a semisolid of desirable consistency and viscosity which can be packed in a single dose container or a seal-a-spoon device of the invention.

EXAMPLE 3

Acetaminophen Formulation Thickened with Carboxymethylcellulose

Acetaminophen (3.2%) is dissolved in a minimum quantity of water; glycerin (4%) and propylene glycol (25%) are added, after which, sodium saccharin (0.2%), methyl parabens (0.22%) and sodium carboxymethylcellulose (2.4%) are incorporated. Water is then added-to make up 100%.

This formulation has a viscosity of 15,000 cps when measured in the same manner as the formulations of Example 1 and has a desirable semisolid consistency useful in packaging in single dose packets or in a multiple dose device of the invention.

EXAMPLE 4

Dextromethorphan Hydrobromide Formulation Thickened with Carbopol™

Dextromethorphan HBr (0.3%) is dissolved in a mixture of propylene glycol (25%), glycerin (4%) and Carbopol 934P (1%) as a thickening agent. Sweetener, preservative, flavor and color as in Example 1 are optionally added and the mixture is made up to 100% with water. This formulation exhibited a viscosity of 15,000 cps, when measured at 20°–21° C. as in Example 1 and had a desirable semisolid consistency suitable for packaging into single dose packets or in a seal-a-spoon device of the invention.

EXAMPLE 5

Dextromethorphan Hydrobromide Formulation Thickened with Gelatin

A pharmaceutical base is prepared by heating gelatin (2.5%) in water. Glycerin (4%), propylene glycol (25%) and dextromethorphan HBr (0.3%) are mixed into the gelatin solution. Sodium saccharin, methyl parabens, flavor and coloring matter are added as in Example 1 and the formulation is made up to 100% with water. This formulation exhibited a viscosity of 7500 which is suitable for packaging into single packets or a seal-a-spoon device of the invention.

The viscosity of this formulation can be increased or decreased within the range of 6000–9000 cps by the addition of more or less gelatin.

EXAMPLE 6

Caridopa/Levidopa Formulation Thickened with Polyethylene Glycols

This is a non-aqueous formulation of caridopa/levidopa, which is useful as an anti-Parkinson medicament containing the following ingredients.

|  | weight %/volume |
| --- | --- |
| Carbidopa | 0.100 |
| Levidopa | 1.000 |
| PEG 400 | 56.524 |
| PEG 3350 | 29.120 |
| Propylene glycol | 13.000 |
| Saccharine Sodium | 0.250 |
| FDC Red #40 | 0.006 |

The formulation, which is prepared by combining the polyethylene glycols with propylene glycol, sweetener and coloring matter and then adding the active agents thereto, has a consistency suitable for use in a single dose packet or in a multiple dose device of the invention.

EXAMPLE 7

Ibuprofen Formulation Thickened with Sodium Carboxymethylcellulose

This semisolid suspension, which contains a non-steroidal anti-inflammatory agent, has the following ingredients and is prepared as indicated in Example 6 by combining the components of the semisolid vehicle and then adding the active constituent thereto.

|  | Weight %/Volume |
| --- | --- |
| Ibuprofen | 2.000 |
| Citric Acid | 0.200 |
| ETDA (Disodium) | 0.020 |
| FDC red #40 | 0.006 |
| Cherry flavor | 0.150 |
| Vanilla flavor | 0.050 |
| Glycerin | 20.000 |
| Sodium carboxymethylcellulose | 2.400 |
| Sodium benzoate | 0.100 |
| Hydrogenated glucose | 6.5 |
| Purified water to | 100 cc |

The consistency of this formulation is suitable for use in a single dose packet or in a multiple dose device of the invention.

EXAMPLE 8

Terfenadine Formulation Thickened with Sodium Carboxymethylcellulose

A semisolid suspension of terfenadine, which is useful for the systemic treatment of allergies, is prepared as in Example 7 with the following ingredients.

|  | Weight %/Volume |
| --- | --- |
| Terfenadine | 0.600 |
| Sodium carboxymethylcellulose | 2.400 |
| Saccharin sodium | 0.250 |
| Hydrogenated glucose | 65.000 |
| Imitation raspberry flavor | 0.150 |
| Methyl paraben | 0.200 |
| Propyl paraben | 0.050 |
| FDC yellow #10 | 0.006 |
| Purified water to | 100 cc |

The consistency of this formulation is suitable for use in a single dose packet or in a multiple dose device of the invention.

EXAMPLE 9

Ranitidine Formulation Thickened with Sodium Carboxymethylcellulose and Hydroxypropyl Methylcellulose A semisolid formulation of ranitidine, which is an antagonist to histamine $H_2$ receptors, is prepared as in Example 7 with the following ingredients.

|  | Weight %/Volume |
| --- | --- |
| Ranitidine HCl | 1.680 |
| (1.5% Ranitidine) |  |
| Dibasic sodium phosphate | 0.030 |
| Sodium carboxymethylcellulose | 2.400 |
| Hydroxypropyl methylcellulose | 0.900 |
| Peppermint flavor | 0.100 |
| FDC yellow #10 | 0.006 |
| Monobasic potassium phosphate | 0.020 |
| Butyl paraben | 0.180 |
| Propyl paraben | 0.500 |
| Sodium chloride | 0.050 |
| Sorbitol 70% | 30.000 |
| Purified water to | 100 cc |

The consistency of this formulation is suitable for use in a single dose packet or in a multiple dose device of the invention.

EXAMPLE 10

Ciprofloxacin HCl Formulation Thickened with Sodium Carboxymethylcellulose

A semisolid formulation of ciprofloxacin HCl, which is an antimicrobic agent, is prepared according to Example 7 with the following ingredients. In this formulation lactic acid is used to solubilize Ciprofloxacin HCl and the pH is adjusted to between 3.5–4.6 with HCl.

|  | Weight %/Volume |
| --- | --- |
| Ciprofloxacin HCl | 10.000 |
| (200 mg Ciprofloxacin) |  |
| Saccharin sodium | 0.250 |
| Lactic acid | 0.020 |
| Sodium carboxymethylcellulose | 2.400 |
| Blackberry flavor | 0.150 |
| FDC red #40 | 0.006 |

-continued

| | Weight %/Volume |
|---|---|
| FDC red #5 | 0.002 |
| Dextrose solution (5%) in purified water to | 100 cc |

The consistency of this formulation is suitable for use in a single dose packet or in a multiple dose device of the invention

EXAMPLE 11

Triazolam Formulation Thickened with Sodium Carboxymethylcellulose

A semisolid formulation of triazolam, a hypnotic useful against insomnia, is prepared according to Example 7 with the following ingredients.

| | Weight %/Volume |
|---|---|
| Triazolam | 0.005 |
| Sodium Benzoate | 0.250 |
| FDC yellow #6 | 0.008 |
| Imitation orange flavor | 0.120 |
| Sodium Saccharin | 0.220 |
| Sodium carboxymethylcellulose | 2.800 |
| Hydrogenated glucose | 20.000 |
| Purified water to | 100 cc |

The consistency of this formulation is suitable for use in a single dose packet or in a multiple dose device of the invention.

EXAMPLE 12

Fluconazole Formulation Thickened with Sodium Carboxymethylcellulose

A semisolid formulation of fluconazole, a broad spectrum antifungal agent, was prepared as in Example 7 with the following ingredients.

| | Weight %/Volume |
|---|---|
| Fluconazole | 2.000 |
| Sodium carboxymethylcellulose | 2.400 |
| FDC red #40 | 0.006 |
| Cherry flavor | 0.150 |
| Sodium saccharin | 0.240 |
| Sodium chloride | 0.050 |
| Purified water to | 100 cc |

The consistency of this formulation is suitable for use in a single dose packet or in a multiple dose device of the invention. The formulation should be stored at a temperature below 25° C., but not lower than 5° C. and must be supplied in a container made of polyvinyl chloride, Baxter Viaflex.

EXAMPLE 13

Acyclovir Formulation Thickened with Sodium Carboxymethylcellulose and Microcrystalline Cellulose A semisolid formulation of acyclovir, an anti-viral agent, is prepared according to Example 7, with the following ingredients.

| | Weight %/Volume |
|---|---|
| Acyclovir | 4.000 |
| Methyl paraben | 0.100 |
| Propyl paraben | 0.020 |
| Sodium carboxymethylcellulose | 2.400 |
| Peppermint flavor | 0.150 |
| Glycerin | 20.000 |
| Microcrystalline cellulose | 0.900 |
| Sorbitol 70% | 20.000 |
| Sodium saccharin | 0.30 |
| FDC yellow #6 | 0.008 |
| Purified water to | 100 cc |

The consistency of this formulation is suitable for use in a single dose packet or in a multiple dose device of the invention.

EXAMPLE 14

Fluoxetine HCl Formulation Thickened with Sodium Carboxymethylcellulose

A semisolid formulation of fluoxetine hydrochloride, and anti-depressant drug, is prepared according to Example 7 with the following ingredients.

| | Weight %/Volume |
|---|---|
| Fluoxetine HCl | 0.400 |
| Benzoic acid | 0.200 |
| Imitation cherry flavor | 0.150 |
| FDC red #40 | 0.006 |
| Glycerin | 30.000 |
| Sodium saccharin | 0.200 |
| Methyl paraben | 0.160 |
| Hydrogenated glucose | 65.000 |
| Sodium carboxymethylcellulose | 2.500 |
| Purified water to | 100 cc |

The consistency of this formulation is suitable for use in a single dose packet or in a multiple dose device of the invention.

EXAMPLE 15

Propranolol HCl Formulation Thickened with Sodium Carboxymethylcellulose and Microcrystalline Cellulose A semisolid formulation of propranolol hydrochloride, which is a synthetic beta adrenergic receptor blocker, is prepared according to Example 7 with the following ingredients.

| | Weight %/Volume | |
|---|---|---|
| | 20 mg/5 cc | 40 mg/5 cc |
| propranolol HCl | 0.400 | 0.800 |
| Cherry flavor | 0.150 | |
| Peppermint flavor | | 0.100 |
| FDC red #40 | 0.006 | |
| FDC yellow #6 | | 0.008 |
| Microcrystalline cellulose | 0.900 | 0.900 |

-continued

|  | Weight %/Volume | |
| --- | --- | --- |
|  | 20 mg/5 cc | 40 mg/5 cc |
| Sodium carboxymethylcellulose | 2.400 | 2.400 |
| Methyl paraben | 0.200 | 0.200 |
| Propyl paraben | 0.050 | 0.050 |
| Sodium saccharin | 0.250 | 0.250 |
| Purified water to | 100 cc | 100 cc |

The consistency of this formulation is suitable for use in a single dose packet or in a multiple dose device of the invention.

EXAMPLE 16

Enalapril Maleate Formulation Thickened with Sodium Carboxymethylcellulose

A semisolid formulation of enalapril maleate, which is useful for treatment of hypertension and heart failure, is prepared according to Example 7 with the following ingredients.

|  | Weight %/Volume |
| --- | --- |
| Enalapril maleate | 0.100 |
| FDC red #40 | 0.007 |
| Saccharin sodium | 0.250 |
| Imitation cherry flavor | 0.150 |
| Sodium carboxymethylcellulose | 2.800 |
| Methyl paraben | 0.220 |
| Purified water to | 200 cc |

The consistency of this formulation is suitable for use in a single dose packet or in a multiple dose device of the invention.

EXAMPLE 17

Diltiazem HCl Formulation Thickened with Sodium Carboxymethylcellulose, Hydroxypropyl Cellulose and Polyethylene Glycol A semisolid formulation of diltiazem hydrochloride, which is a calcium antagonist, is prepared according to Example 7 with the following ingredients.

|  | Weight %/Volume |
| --- | --- |
| Diltiazem HCl | 0.600 |
| FDC yellow #6 | 0.006 |
| Peppermint flavor | 0.100 |
| Hydroxypropyl cellulose | 0.900 |
| Sodium carboxymethylcellulose | 2.400 |
| Hydrogenated glucose | 60.000 |
| Saccharin sodium | 0.220 |
| Polyethylene glycol 1500 | 10.000 |
| Purified water to | 100 cc |

The consistency of this formulation is suitable for use in a single dose packet or in a multiple dose device of the invention.

EXAMPLE 18

Lovastatin Formulation Thickened with Sodium Carboxymethylcellulose and Polyethylene glycol A semisolid formulation of lovastatin, a cholesterol lowering agent, is prepared according to Example 7 with the following ingredients.

|  | Weight %/Volume |
| --- | --- |
| Lovastatin | 0.200 |
| Butylhydroxy toluene | 0.200 |
| Sodium carboxymethylcellulose | 2.500 |
| FDC red #40 | 0.006 |
| Peppermint flavor | 0.100 |
| Sodium saccharin | 0.250 |
| Polyethylene glycol 1500 | 25.000 |
| Methyl paraben | 0.200 |
| Purified water to | 100 cc |

What I desire to claim and protect by letters patent is:

1. A pharmaceutical delivery system for oral administration of a pharmaceutical agent, comprising:

(a) a squeezable container having an outlet defining a flow channel, (b) a channel closure device adapted to selectively close or open the flow channel; and (c) within the container, at least one dose of a pharmaceutical composition, the composition being a semisolid material that is storage stable, and consists of mutually compatible components, the components comprising
(i) an effective amount of an orally active pharmaceutical agent useful for systemic treatment, and
(ii) a palatable pharmaceutically acceptable vehicle, comprising
a liquid base selected from the group consisting of water, propylene glycol, polyethylene glycol, glycerin, and mixtures thereof,
a thickening agent selected from the group consisting of starch, modified starch, sodium carboxymethyl cellulose, microcrystalline cellulose, hydroxypropyl cellulose, hydroxypropyl methylcellulose, other cellulose derivatives, acacia, tragacanth, pectin, gelatin, polyethylene glycol, and water-soluble carboxyvinyl polymers, the pharmaceutical composition having a consistency which allows the composition to be squeezed by manual pressure through the flow channel, whereby in response to pressure on the container when the flow channel is open, a predetermined unit dose of the pharmaceutical composition can be easily squeezed from the container into a receptacle, measured, and administered orally without spilling any of the composition from the container or the receptacle.

2. A system according to claim 1 wherein the composition further comprises hydrogenated glucose in an amount greater than about 6.5%.

3. A system according to claim 1 wherein the vehicle consists essentially of the liquid base, the thickening agent, and optionally sweetener, flavoring, preservative, buffer, and solubilizing agent.

4. A system according to claim 1 wherein the composition has a Brookfield viscosity of about 7500 to about 40,000 cps at about 25° C. at a spindle speed of 10 rpm.

5. A system according to claim 1 wherein the container is a flexible tube.

6. A system according to claim 1 further comprising a receptacle positioned to receive material dispensed from the channel, whereby the configuration of the container, channel closure device, and receptacle and the consistency of the formulation are selected so that in response to pressure on the container when the flow channel is open, a predetermined unit dose of the pharmaceutical composition can be easily squeezed by manual pressure from the container through the flow channel into the receptacle, measured, and administered orally without spilling any of the composition from the container or the receptacle.

7. A system according to claim 6, wherein the receptacle is a spoon bowl connected to the container positioned at the flow channel, sized to hold a unit dose of the pharmaceutical composition.

8. The system of claim 1, wherein the liquid base comprises propylene glycol and glycerin, and the thickening agent comprises a water soluble carboxyvinyl polymer.

9. The system of claim 8, wherein the concentration of propylene glycol and glycerin is about 29%, and the concentration of the carboxyvinyl polymer is up to about 1%.

10. The system of claim 1, wherein the liquid base comprises glycerin and sorbitol, and the thickening agent comprises sodium carboxymethylcellulose and microcrystalline cellulose.

11. The system of claim 10, wherein the sorbitol is present as a solution of about 70% in water, the concentration of glycerin and sorbitol solution is about 40%, the concentration of the carboxymethylcellulose is about 2.4%, and the concentration of the microcrystalline cellulose is about 0.9%.

12. The system of claim 1, in which the channel closure device comprises a valve.

13. The pharmaceutical delivery system of claim 1, wherein the liquid base is in an amount of about 45 weight-percent to about 95 weight-percent, and the thickening agent is an amount of about 1 weight-percent to about 55 weight-percent.

14. The system of claim 1, wherein the liquid base is selected from water, propylene glycol, glycerin or a mixture thereof.

15. The system of claim 1, comprising multidoses of the pharmaceutical composition.

16. The system of claim 1, wherein the thickening agent is a cellulose derivative in an amount of about 2.4 to 3.3 weight % by volume.

17. The system of claim 1, wherein the thickening agent is a polyethylene glycol in an amount of about 72 to 85 weight % by volume or a mixture of polyethylene glycol in an amount of about 10 to 25 weight % by volume and a cellulose derivative in an amount of about 2.5 to 3.3 weight % by volume.

18. The system of claim 1, wherein, the pharmaceutical agent is selected from a member of the group consisting of an analgesic, non-steroidal anti-inflammatory, antihistamine, cough suppressant, expectorant, bronchodilator, anti-infective, CNS active drug, cardiovascular drug, antineoplastic, cholesterol-lowering drug, anti-emetic, vitamin, mineral supplement and fecal softener.

19. The system of claim 1, wherein the pharmaceutical agent is selected from a member of the group consisting of acetaminophen, aspirin, ibuprofen, diphenhydramine, dextromethorphan, quafenesin, pseudoephedrine, carbidopa, levodopa, terfenadine, ranitidine, ciprofloxacin, triazolam, fluconazole, propranolol, acyclovir, fluoxetine, enalapril, diltiazem, lovastatin and a pharmaceutically acceptable salt or ester thereof.

20. A system according to claim 1 wherein the composition has a Brookfield viscosity of 2500 to 70,000 cps.

21. A system according to claim 1 wherein the composition has a Brookfield viscosity of 3500 to 65,000 cps.

22. A system according to claim 1 wherein the composition has a Brookfield viscosity of 6000 to 9000 cps.

23. A system according to claim 1 wherein the composition has a Brookfield viscosity of 7500 to 40,000 cps.

24. A system according to claim 1 wherein the liquid base comprises propylene glycol in an amount up to 25%.

25. A system according to claim 1 wherein the liquid base comprises glycerin in an amount of 4% to 30%.

26. A system according to claim 1 wherein the thickening agent comprises 1% of a water-soluble carboxyvinyl polymer.

27. A system according to claim 1 wherein the pharmaceutical agent is dissolved.

28. A system according to claim 1 wherein the pharmaceutical agent is suspended.

29. The system of claim 8, wherein the concentration of the carboxyvinyl polymer is 1%.

30. A pharmaceutical delivery system comprising:
(a) at least one dose of a storage stable, semisolid pharmaceutical composition comprising an effective amount of a pharmaceutical agent useful for systemic treatment in a pharmaceutically acceptable vehicle, the vehicle comprising a liquid base and a thickening agent in an amount effective to provide a Brookfield viscosity of about 2500 to 70,000 cps at about 25° C. and a spindle speed of about 10 rpm;
(b) means for containing and dispensing substantially all of the pharmaceutical composition upon manual pressure; and
(c) means for dispensing the composition connected to the container means, the dispensing means comprising a channel communicating with the containing means and having an internal diameter of from about 0.1 mm to about 5 mm, and means for reversibly sealing the channel, having sealed and open positions.

31. The delivery system of claim 30, further comprising means for receiving a unit dose of the composition, whereby in response to pressure on the means for containing, when the sealing means is in the open position, a predetermined unit dose of the pharmaceutical composition can be easily squeezed into the receiving means, measured, and administered orally without spilling any of the composition from the containing means or the receiving means.

32. The system of claim 31, wherein the receptacle is a spoon bowl attached to the dispenser.

33. A system according to claim 30 wherein the composition has a Brookfield viscosity of 3500 to 65,000 cps.

34. A system according to claim 30 wherein the composition has a Brookfield viscosity of 6000 to 9000 cps.

35. A system according to claim 30 wherein the composition has a Brookfield viscosity of 7500 to 40,000 cps.

36. A system according to claim 30 wherein the pharmaceutical agent is dissolved.

37. A system according to claim 30 wherein the pharmaceutical agent is suspended.

38. A system according to claim 30 wherein the liquid base comprises propylene glycol.

39. A system according to claim 30, wherein the liquid base comprises propylene glycol in an amount up to 25%.

40. A system according to claim 30 wherein the liquid base comprises glycerin.

41. A system according to claim 30 wherein the liquid base comprises glycerin in an amount of 4% to 30%.

42. A system according to claim 30 wherein the liquid base is selected from the group consisting of water, propylene glycol, polyethylene glycol, glycerin, and mixtures thereof.

43. A system according to claim 30 wherein the thickening agent is selected from the group consisting of starch, modified starch, sodium carboxymethyl cellulose, microcrystalline cellulose, hydroxypropyl cellulose, hydroxypropyl methylcellulose, other cellulose derivatives, acacia, tragacanth, pectin, gelatin, polyethylene glycol, and water-soluble carboxyvinyl polymers.

44. A system according to claim 30, wherein the composition comprises hydrogenated glucose and/or sorbitol.

45. A system according to claim 30 wherein the thickening agent comprises 1% of a water-soluble carboxyvinyl polymer.

46. The system of claim 30, wherein, the pharmaceutical agent is selected from a member of the group consisting of an analgesic, non-steroidal anti-inflammatory, antihistamine, cough suppressant, expectorant, bronchodilator, anti-infective, CNS active drug, cardiovascular drug, antineoplastic, cholesterol-lowering drug, antiemetic, and fecal softener.

47. The system of claim 30, wherein the pharmaceutical agent is selected from a member of the group consisting of acetaminophen, aspirin, ibuprofen, diphenhydramine, dextromethorphan, guaifenesin, pseudoephedrine, carbidopa, levodopa, terfenadine, ranitidine, ciprofloxacin, triazolam, fluconazole, propranolol, acyclovir, fluoxetine, enalapril, diltiazem, lovastatin and a pharmaceutically acceptable salt or ester thereof.

* * * * *